(12) United States Patent
Crouzet et al.

(10) Patent No.: US 6,287,762 B1
(45) Date of Patent: Sep. 11, 2001

(54) PURIFICATION OF A TRIPLE HELIX FORMATION WITH AN IMMOBILIZED OLIGONUCLEOTIDE

(75) Inventors: Joël Crouzet, Sceaux; Daniel Scherman; Pierre Wils, both of Paris, all of (FR)

(73) Assignee: Rhone-Poulenc Rorer S.A., Antony Cedex (FR)

( * ) Notice: Subject to any disclaimer, the term of this patent is extended or adjusted under 35 U.S.C. 154(b) by 0 days.

(21) Appl. No.: 08/860,038

(22) PCT Filed: Nov. 8, 1995

(86) PCT No.: PCT/FR95/01468

§ 371 Date: Jun. 9, 1997

§ 102(e) Date: Jun. 9, 1997

(87) PCT Pub. No.: WO96/18744

PCT Pub. Date: Jun. 20, 1996

(30) Foreign Application Priority Data

Dec. 16, 1994 (FR) .................................................. 94/15162

(51) Int. Cl.[7] .................................. C12Q 1/68; C12P 19/34
(52) U.S. Cl. ................................................ 435/6; 435/91.2
(58) Field of Search ........................................ 435/6, 91.2

(56) References Cited

U.S. PATENT DOCUMENTS

| 4,766,072 | 8/1988 | Jendrisak et al. | 435/91 |
|---|---|---|---|
| 5,401,632 | 3/1995 | Wang et al. | 435/6 |
| 5,665,541 | 9/1997 | Miller et al. | 435/6 |

FOREIGN PATENT DOCUMENTS

| 89/02436 | 3/1989 | (WO) . |
|---|---|---|
| 90/09393 | 8/1990 | (WO) . |
| 90/10716 | 9/1990 | (WO) . |
| WO 92/09705 | 6/1992 | (WO) . |
| 92/11390 * | 7/1992 | (WO) . |
| WO 92/13963 | 8/1992 | (WO) . |
| 92/18647 | 10/1992 | (WO) . |
| WO 93/00352 | 1/1993 | (WO) . |
| 93/13220 | 7/1993 | (WO) . |
| 94/00600 | 1/1994 | (WO) . |
| WO 94/17086 | 8/1994 | (WO) . |

OTHER PUBLICATIONS

Ito et al, PNAS 89:495–498, 1992.*
Ausubel et al., Large–Scale Preparation of Plasmid DNA, Current Protocols in Molec. Biol., Supp. 27, 1.7.1–1.7.15 (1994).
Ausubel et al., Minipreps of Plasmid DNA, Current Protocols in Molec. Biol., Supp. 15, 1.6.1–1.6.10 (1991).
Sambrook et al., Extraction and Purification of Plasmid DNA, Laboratory Manual, 1.21–1.52 (1987).
He et al., An Improved and Rapid Procedure for Isolating RNA–Free *Escherichia coli* Plasmid DNA, Genetic Analysis Techniques & Applications, 8(3) 107–110 (1991).
Ito et al., Sequence–specific DNA purification by triplex affinity capture, Proc. Natl. Acad. Sci. USA, 89, 495–498 (1992).
Jarrett, Affinity chromatography with nucleic acid polymers, Journal of Chromatography, 618(8), 315–339 (1993).
Kiessling et al., Flanking Sequence Effects within the Pyrimidine Triple–Helix Motif Characterized by Affinity Cleaving, Biochemistry, 31, 2829–2834 (1992).
Duval–Valentin et al., Specific Inhibition of Trancription by Triple Helix–Forming Oligonucleotides, Proc. Natl. Acad. Sci., USA, 89, 504–508 (1992).
Jayasena et al., Oligonucleotide–directed triple helix formation at adjacent oligopurine and oligopyrimidine DNA tracts by alternate strand recognition, Nucleic Acids Research, 20(20), 5279–5288 (1992).

* cited by examiner

*Primary Examiner*—Eggerton A. Campbell

(57) ABSTRACT

Method for double-stranded DNA purification, by which a solution containing said DNA in a mixture with other components is passed over a support on which is covalently coupled in oligonucleotide capable of hybridizing with a specific sequence present on said DNA to form a triple helix.

41 Claims, No Drawings

PURIFICATION OF A TRIPLE HELIX FORMATION WITH AN IMMOBILIZED OLIGONUCLEOTIDE

This application claims the benefit of foreign priority under 35 U.S.C. § 119 to application FR 94/15162 which was filed Dec. 16, 1994. This application is a 371 of PCT/FR95/01468, filed Nov. 8, 1995.

The present invention relates to a new method for DNA purification. The method according to the invention enables pharmacologically usable double-stranded DNA to be purified rapidly. More especially, the purification method according to the invention involves a specific hybridization between a sequence of the DNA and an oligonucleotide.

Gene and cell therapy techniques are currently undergoing remarkable development. However, these techniques entail the possibility of producing large amounts of DNA of pharmaceutical purity. In effect, in these new therapies, the medicament often consists of DNA itself, and it is essential to be able to manufacture it in suitable amounts, to isolate it and to purify it in a manner suited to therapeutic use in man.

The present invention describes a simple and especially effective new method for DNA purification. It makes it possible, in particular, to obtain especially high purities with high yields.

The method according to the invention is based essentially on a specific interaction between a sequence inserted into the DNA to be purified and an oligonucleotide composed of natural or modified bases.

It has recently been shown that some oligonucleotides are capable of interacting specifically in the wide groove of the DNA double helix to form triple helices locally, leading to an inhibition of the transcription of target genes (Hélène et Toulmé, Biochim. Biophys. Acta 1049 (1990) 99). These oligonucleotides selectively recognize the DNA double helix at oligopurine-oligopyrimidine sequences, that is to say at regions possessing an oligopurine sequence on one strand and an oligopyrimidine sequence on the complementary strand, and form a triple helix locally thereat. The bases of the third strand (the oligonucleotide) form hydrogen bonds (Hoogsteen or reverse Hoogsteen bonds) with the purines of the Watson-Crick base pairs.

A use of this type of interaction to isolate a plasmid has been described in the prior art. Thus, Ito et al. (PNAS 89 (1992) 495) describe the use of biotinylated oligonucleotides capable of recognizing a particular sequence of a plasmid and of forming a triple helix therewith. The complexes thus formed are then brought into contact with streptavidin-coated magnetic beads. Interaction between the biotin and the streptavidin then enables the plasmid to be isolated by magnetic separation of the beads followed by elution. However, this method has some drawbacks. In particular, two successive specific interactions are needed, the first between the oligonucleotide and the plasmid and the second between the biotinylated complex and the streptavidin beads. Furthermore, the final solution may be contaminated with biotinylated oligonucleotide, which cannot be used in a pharmaceutical composition.

The present invention describes a new, improved method of DNA purification making use of this type of interaction. More especially, the method of the invention employs oligonucleotides coupled covalently to a support. This method is especially rapid, and it leads to especially high yields and degrees of purity. Moreover, it enables DNA to be purified from complex mixtures comprising, in particular, other nucleic acids, proteins, endotoxins (such as lipopolysaccharides), nucleases and the like. The supports used may, in addition, be readily recycled, and the DNAs obtained display improved properties of pharmaceutical safety. Lastly, this method entails only one step, contrary to the prior art.

Hence a first subject of the invention lies in a method for the purification of double-stranded DNA, according to which a solution containing the said DNA mixed with other components is passed through a support to which is coupled covalently an oligonucleotide capable of forming a triple helix by hybridization with a specific sequence present in said DNA. The specific sequence can be a sequence naturally present in the double-stranded DNA, or a synthetic sequence introduced artificially into the latter.

The oligonucleotides used in the present invention are oligonucleotides which hybridize directly with the double-stranded DNA. These oligonucleotides can contain the following bases:

thymidine (T), which is capable of forming triplets with A.T doublets of double-stranded DNA (Rajagopal et al., Biochem 28 (1989) 7859);

adenine (A), which is capable of forming triplets with A.T doublets of double-stranded DNA;

guanine (G), which is capable of forming triplets with G.C doublets of double-stranded DNA;

protonated cytosine (C+), which is capable of forming triplets with G.C doublets of double-stranded DNA (Rajagopal et al., loc. cit.);

uracil (U), which is capable of forming triplets with A.U or A.T base pairs.

Preferably, the oligonucleotide used comprises a cytosine-rich homopyrimidine sequence and the specific sequence present in the DNA is a homopurine-homopyrimidine sequence. The presence of cytosines makes it possible to have a triple helix which is stable at acid pH where the cytosines are protonated, and destabilized at alkaline pH where the cytosines are neutralized.

To permit the formation of a triple helix by hybridization, it is important for the oligonucleotide and the specific sequence present in the DNA to be complementary. In this connection, to obtain the best yields and the best selectivity, an oligonucleotide and a specific sequence which are fully complementary are used in the method of the invention. These can be, in particular, an oligonucleotide poly(CTT) and a specific sequence poly(GAA). As an example, there may be mentioned the oligonucleotide of sequence 5'-GAGGCTTCTTCTTCTTCTTCTTCTT-3' (GAGG (CTT)$_7$; SEQ ID No. 1), in which the bases GAGG do not form a triple helix but enable the oligonucleotide to be spaced apart from the coupling arm; the sequence (CTT)$_7$ (SEQ ID No. 26) may also be mentioned. These oligonucleotides are capable of forming a triple helix with a specific sequence containing complementary units (GAA). The sequence in question can, in particular, be a region containing 7, 14 or 17 GAA units, as described in the examples.

Another sequence of specific interest is the sequence: 5'-AAGGGAGGGAGGAGAGGAA-3' (SEQ ID No. 5). This sequence forms a triple helix with the oligonucleotides 5'-AAGGAGGAGGGAGGGAA-3' (SEQ ID No. 6) or 5'-TTGGTGTGGTGGGTGGGTT-3' (SEQ ID No. 7).

In this case, the oligonucleotide binds in an antiparallel orientation to the polypurine strand. These triple helices are stable only in the presence of $Mg^{2+}$ (Vasquez et al., Biochemistry, 1995, 34, 7243–7251; Beal and Dervan, Science, 1991, 251, 1360–1363).

As stated above, the specific sequence can be a sequence naturally present in the double-stranded DNA, or a synthetic sequence introduced artificially in the latter. It is especially advantageous to use an oligonucleotide capable of forming a triple helix with a sequence naturally present in the double-stranded DNA, for example in the origin of replication of a plasmid or in a marker gene. In this connection, the Applicant has performed plasmid sequence analyses, and was able to show that some regions of these DNAs, in particular in the origin of replication, could possess homopurine-homopyrimidine regions. The synthesis of oligonucleotides capable of forming triple helices with these natural homopurine-homopyrimidine regions advantageously enables the method of the invention to be applied to unmodified plasmids, in particular commercial plasmids of the pUC, pBR322, pSV, and the like, type. Among the homopurine-homopyrimidine sequences naturally present in a double-stranded DNA, a sequence comprising all or part of the sequence 5'-CTTCCCGAAGGGAGAAAGG-3' (SEQ ID No. 2) present in the E. coli origin of replication ColE1 may be mentioned. In this case, the oligonucleotide forming the triple helix possesses the sequence:

5'-GAAGGGTTCTTCCCTCTTTCC-3' (SEQ ID No. 3), and binds alternately to the two strands of the double helix, as described by Beal and Dervan (J. Am. Chem. Soc. 1992, 114, 4976–4982) and Jayasena and Johnston (Nucleic Acids Res. 1992, 20, 5279–5288). The sequence 5'-GAAAAAGGAAGAG-3' (SEQ ID No. 4) of the plasmid pBR322 β-lactamase gene (Duval-Valentin et al., Proc. Natl. Acad. Sci. USA, 1992, 89, 504–508) may also be mentioned. The use of an oligonucleotide capable of forming a triple helix with a sequence present in an origin of replication or a marker gene is especially advantageous, since it makes it possible, with the same oligonucleotide, to purify any DNA containing the said origin of replication or said marker gene. Hence it is not necessary to modify the plasmid or the double-stranded DNA in order to incorporate an artificial specific sequence in it.

Although fully complementary sequences are preferred, it is understood, however, that some mismatches may be tolerated between the sequence of the oligonucleotide and the sequence present in the DNA, provided they do not lead to too great a loss of affinity. The sequence 5'-AAAAAAGGGAATAAGGG-3' (SEQ ID No. 8) present in the E. coli β-lactamase gene may be mentioned. In this case, the thymine interrupting the polypurine sequence may be recognized by a guanine of the third strand, thereby forming an ATG triplet which it is stable when flanked by two TAT triplets (Kiessling et al., Biochemistry, 1992, 31, 2829–2834).

According to a particular embodiment, the oligonucleotides of the invention comprise the sequence $(CCT)_n$, the sequence $(CT)_n$ or the sequence $(CTT)_n$, in which n is an integer between 1 and 15 inclusive. It is especially advantageous to use sequences of the type $(CT)_n$ or $(CTT)_n$. The Applicant showed, in effect, that the purification yield was influenced by the amount of C in the oligonucleotide. In particular, as shown in Example 7, the purification yield increases when the oligonucleotide contains fewer cytosines. It is understood that the oligonucleotides of the invention can also combine (CCT), (CT) or (CTT) units.

The oligonucleotide used may be natural (composed of unmodified natural bases) or chemically modified. In particular, the oligonucleotide may advantageously possess certain chemical modifications enabling its resistance to or its protection against nucleases, or its affinity for the specific sequence, to be increased.

According to the present invention, oligonucleotide is also understood to mean any linked succession of nucleosides which has undergone a modification of the skeleton with the aim of making it more resistant to nucleases. Among possible modifications, oligonucleotide phosphorothioates, which are capable of forming triple helices with DNA (Xodo et al., Nucleic Acids Res., 1994, 22, 3322–3330), as well as oligonucleotides possessing formacetal or methylphosphonate skeletons (Matteucci et al., J. Am. Chem. Soc., 1991, 113, 7767–7768), may be mentioned. It is also possible to use oligonucleotides synthesized with α anomers of nucleotides, which also form triple helices with DNA (Le Doan et al., Nucleic Acids Res., 1987, 15, 7749–7760). Another modification of the skeleton is the phosphoramidate link. For example, the $N^{3'}$-$P^{5'}$ internucleotide phosphoramidate link described by Gryaznov and Chen, which gives oligonucleotides forming especially stable triple helices with DNA (J. Am. Chem. Soc., 1994, 116, 3143–3144), may be mentioned. Among other modifications of the skeleton, the use of ribonucleotides, of 2'-O-methylribose, phosphodiester, etc. (Sun and Hélène, Curr. Opinion Struct. Biol., 116, 3143–3144) may also be mentioned. Lastly, the phosphorus-based skeleton may be replaced by a polyamide skeleton as in PNAs (peptide nucleic acids), which can also form triple helices (Nielsen et al., Science, 1991, 254, 1497–1500; Kim et al., J. Am. Chem. Soc., 1993, 115, 6477–6481)), or by a guanidine-based skeleton, as in DNGs (deoxyribonucleic guanidine, Proc. Natl. Acad. Sci. USA, 1995, 92, 6097–6101), polycationic analogues of DNA, which also form triple helices.

The thymine of the third strand may also be replaced by a 5-bromouracil, which increases the affinity of the oligonucleotide for DNA (Povsic and Dervan, J. Am. Chem. Soc., 1989, 111, 3059–3061). The third strand may also contain unnatural bases, among which there may be mentioned 7-deaza-2'-deoxyxanthosine (Milligan et al., Nucleic Acids Res., 1993, 21, 327–333), 1-(2-deoxy-β-D-ribofuranosyl)-3-methyl-5-amino-1H-pyrazolo[4,3-d]pyrimidin-7-one (Koh and Dervan, J. Am. Chem. Soc., 1992, 114, 1470–1478), 8-oxoadenine, 2-aminopurine, 2'-O-methylpseudoisocytidine, or any other modification known to a person skilled in the art (for a review see Sun and Hélène, Curr. Opinion Struct. Biol., 1993, 3, 345–356).

Another type of modification of the oligonucleotide has the aim, more especially, of improving the interaction and/or affinity between the oligonucleotide and the specific sequence. In particular, a most advantageous modification according to the invention consists in methylating the cytosines of the oligonucleotide (see Example 5). The oligonucleotide thus methylated displays the noteworthy property of forming a stable triple helix with the specific sequence in pH ranges closer to neutrality ($\geq 5$). It hence makes it possible to work at higher pH values than the oligonucleotides of the prior art, that is to say at pH values where the risks of degradation of plasmid DNA are much smaller.

The length of the oligonucleotide used in the method of the invention is at least 3 bases, and preferably between 5 and 30. An oligonucleotide of length greater than 10 bases is advantageously used. The length may be adapted by a person skilled in the art for each individual case to suit the desired selectivity and stability of the interaction.

The oligonucleotides according to the invention may be synthesized by any known technique. In particular, they may be prepared by means of nucleic acid synthesizers. Any other method known to a person skilled in the art may quite obviously be used.

To permit its covalent coupling to the support, the oligonucleotide is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the oligonucleotide and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the oligonucleotide at a chosen distance from the support, enabling its conditions of interaction with the DNA to be improved. The arm advantageously consists of a linear carbon chain, comprising 1 to 18 and preferably 6 or 12 ($CH_2$) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used. These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

To obtain better purification yields, it is especially advantageous to use, on the plasmid, a sequence containing several positions of hybridization with the oligonucleotide. The presence of several hybridization positions promotes, in effect, the interactions between the said sequence and the oligonucleotide, which leads to an improvement in the purification yields. Thus, for an oligonucleotide containing n repeats of (CCT), (CT) or (CTT) motifs, it is preferable to use a DNA sequence containing at least n complementary motifs, and preferably n+1 complementary motifs. A sequence carrying n+1 complementary motifs thus affords two positions of hybridization with the oligonucleotide. Advantageously, the DNA sequence contains up to 11 hybridization positions, that is to say n+10 complementary motifs.

The method according to the present invention can be used to purify any type of double-stranded DNA. An example of the latter is circular DNA, such as a plasmid, generally carrying one or more genes of therapeutic importance. This plasmid may also carry an origin of replication, a marker gene, and the like. The method of the invention may be applied directly to a cell lysate. In this embodiment, the plasmid, amplified by transformation followed by cell culture, is purified directly after lysis of the cells. The method of the invention may also be applied to a clear lysate, that is to say to the supernatant obtained after neutralization and centrifugation of the cell lysate. It may quite obviously be applied also to a solution prepurified by known methods. This method also enables linear or circular DNA carrying a sequence of importance to be purified from a mixture comprising DNAs of different sequences. The method according to the invention can also be used for the purification of double-stranded DNA.

The cell lysate can be a lysate of prokaryotic or eukaryotic cells.

As regards prokaryotic cells, the bacteria *E. coli, B. subtilis, S. typhimurium* or Strepomyces may be mentioned as examples. As regards eukaryotic cells, animal cells, yeasts, fungi, and the like, may be mentioned, and more especially Kluyveromyces or Saccharomyces yeasts or COS, CHO, C127, NIH3T3, and the like, cells.

The method of the invention is especially advantageous, since it enables plasmid DNA of very high purity to be obtained rapidly and simply. In particular, as illustrated in the examples, this method enables the plasmid DNA in question to be separated effectively from contaminating components such as fragmented chromosomal DNA, endotoxins, proteins, nucleases, and the like. More especially, the method of the invention enables preparation of double-stranded DNA, in particular that of plasmid origin, having a chromosomal DNA content of less than or equal to 0.5% to be obtained. Still more preferably, the DNA preparations obtained have a chromosomal DNA content of less than or equal to 0.2%. The present invention hence describes compositions comprising plasmid DNA which can be used pharmaceutically, in particular in gene or cell therapy. In this connection, the subject of the invention is also a pharmaceutical composition comprising double-stranded DNA, linear or of plasmid origin, prepared according to the method described above.

The invention also relates to plasmid DNA preparations having a chromosomal DNA content of less than or equal to 0.5%, preferably less than or equal to 0.2% and still more preferably less than or equal to 0.1%.

The compositions can contain plasmid DNA which is "naked" or combined with transport carriers such as liposomes, nanoparticles, cationic lipids, polymers, recombinant viruses or proteins, and the like.

The present application will be described in greater detail by means of the examples which follow, which are to be regarded as illustrative and non-limiting.

General techniques of cloning and molecular biology

The traditional methods of molecular biology, such as digestion with restriction enzymes, gel electrophoresis, transformation in *E. coli*, precipitation of nucleic acids and the like, are described in the literature (Maniatis et al., T., E. F. Fritsch, and J. Sambrook, 1989. Molecular cloning: a laboratory manual, second edition. Cold Spring Harbor Laboratory, Cold Spring Harbor Laboratory Press, New York; Ausubel F. M., R. Brent, R. E. Kinston, D. D. Moore, J. A. Smith, J. G. Seidman and K. Struhl. 1987. Current protocols in molecular biology 1987–1988. John Willey and Sons, New York.). Nucleotide sequences were determined by the chain termination method according to the protocol already published (Ausubel et al., 1987).

Restriction enzymes were supplied by New England Biolabs, Beverly, Mass. (Biolabs).

To carry out ligations, DNA fragments are incubated in a buffer comprising 50 mM Tris-HCl pH 7.4, 10 mM $MgCl_2$, 10 mM DTT, 2 mM ATP in the presence of phage T4 DNA ligase (Biolabs).

Oligonucleotides are synthesized using phosphoramidite chemistry with the phosphoramidites protected at the β position by a cyanoethyl group (Sinha, N. D., J. Biernat, J. McManus and E. Köster, 1984. Polymer support oligonucleotide synthesis, XVIII: Use of β-cyanoethyl-N,N- dialkylamino-/N-morpholino phosphoramidite of deoxynucleosides for the synthesis of DNA fragments simplifying deprotection and isolation of the final product. Nucl. Acids Res., 12, 4539–4557: Giles, J. W. 1985. Advances in automated DNA synthesis. Am. Biotechnol., Nov./Dec.) with a Biosearch 8600 automatic DNA synthesizer, using the manufacturer's recommendations.

Ligated DNAs or DNAs to be tested for their efficacy of transformation are used to transform the following strain rendered competent:

E. coliDH5α[F/endA1, hsdR17, supE44, thi-1, recA1, gyrA96, relA1, Δ(lacZYA-argF)U169, deoR, φ80dlac (lacZΔM15)]

Minipreparations of plasmid DNA are made according to the protocol of Klein et al., 1980.

LB culture medium is used for the growth of E. coli strains (Maniatis et al., 1982). Strains are incubated at 37° C. Bacteria are plated out on dishes of LB medium supplemented with suitable antibiotics.

EXAMPLE 1

1.1. Preparation of the column

Equipment

The column used is a 1 ml HiTrap column activated with NHS (N-hydroxysuccinimide, Pharmacia) connected to a peristaltic pump (output <1 ml/min. The specific oligonucleotide used possesses an $NH_2$ group at the 5' end, its sequence is as follows:

5'-GAGGCTTCTTCTTCTTCTTCTTCTT-3' (SEQ ID No. 1)

The buffers used in this example are the following:

Coupling buffer: 0.2 M $NaHCO_3$, 0.5 M NaCl, pH 8.3.
Buffer A: 0.5 M ethanolamine, 0.5 M NaCl, pH 8.3.
Buffer B: 0.1 M acetate, 0.5 M NaCl, pH 4.

Method:

The column is washed with 6 ml of 1 mM HCl, and the oligonucleotide diluted in the coupling buffer (50 nmol in 1 ml) is then applied to the column and left for 30 minutes at room temperature. The column is washed three times in succession with 6 ml of buffer A and then 6 ml of buffer B. The oligonucleotide is thus bound covalently to the column through a CONH link. The column is stored at 4° C. in PBS, 0.1% $NaN_3$, and may be used at least four times.

1.2. Construction of plasmids

The following two oligonucleotides were synthesized. oligonucleotide 4817:

5'-GATCCGAAGAAGAAGAAGAAGAAGAAGAAG-AAGAAGAAGAAGAAGAA GAAGAAGG-3' (SEQ ID No. 9)

oligonucleotide 4818:

5'-AATTCCTTCTTCTTCTTCTTCTTCTTCTTCT-TCTTCTTCTTCTTCTTCT TCG-3' (SEQ ID No. 10)

These oligonucleotides, when hybridized and cloned into a plasmid, introduce a homopurine-homopyrimidine sequence $(GAA)_{17}$ into the corresponding plasmid, as described above.

The sequence corresponding to these two hybridized oligonucleotides was cloned at the multiple cloning site of plasmid pBKS+(Stratagene Cloning System, La Jolla, Calif.), which carries an ampicillin-resistance gene. To this end, the oligonucleotides were hybridized in the following manner: one μg of these two oligonucleotides were placed together in 40 ml of a final buffer comprising 50 mM Tris-HCl pH 7.4, 10 mM $MgCl_2$. This mixture was heated to 95° C. and was then placed at room temperature so that the temperature would fall slowly. Ten ng of the mixture of hybridized oligonucleotides were ligated with 200 ng of plasmid pBKS+ (Stratagene Cloning System, La Jolla, Calif.) digested with BamHI and EcoRI in 30 μl final. After ligation, an aliquot was transformed into DH5a. The transformation mixtures were plated out on L medium supplemented with ampicillin (50 mg/l) and X-gal (20 mg/l). The recombinant clones should display an absence of blue colouration on this medium, contrary to the parent plasmid (pBKS+) which permits α-complementation of fragment ω of E. coli β-galactosidase. After minipreparation of plasmid DNA from 6 clones, they all displayed the disappearance of the PstI site located between the EcoRI and BamHI sites of pBKS+, and an increase in molecular weight of the 448-bp PvuII band containing the multiple cloning site. One clone was selected and the corresponding plasmid was designated pXL2563. The cloned sequence was verified by sequencing using primer -20 (5'-TGACCGGCAGCAAAATG-3' (SEQ ID No. 11)) (Viera J. and J. Messing. 1982. The pUC plasmids, an M13mp7-derived system for insertion mutagenesis and sequencing with synthetic universal primers. Gene, 19, 259–268) for plasmid pBKS+ (Stratagene Cloning System, La Jolla, Calif.). Plasmid pXL2563 was purified according to Wizard Megaprep kit (Promega Corp. Madison, Wis.) according to the supplier's recommendations. This plasmid DNA preparation was used thereafter in examples described below.

1.3. Plasmid purification

Equipment:

Plasmid pXL2563 (described in 1.2) was purified on the HiTrap column coupled to the oligonucleotide, described in 1.1., from a solution also containing plasmid pBKS+. The buffers used in this purification are the following:

Buffer F: 2 M NaCl, 0.2 M acetate, pH 4.5 to 5.
Buffer E: 1 M Tris-HCl, pH 9, 0.5 mM EDTA.

Method:

The column is washed with 6 ml of buffer F, and the plasmids (20 μg of pXL2563 and 20 μg of pBKS+ in 400 μl of buffer F) are applied to the column and incubated for 2 hours at room temperature. The column is washed with 10 ml of buffer F and elution is then carried out with buffer E. The plasmids are detected after electrophoresis on 1% agarose gel and ethidium bromide staining. The proportion of the plasmids in the solution is estimated by measuring their transforming activity on E. coli.

Result:

Starting from a mixture containing 30% of pXL2563 and 70% of pBKS+, a solution containing 100% of pXL2563 is recovered at the column outlet. The purity, estimated by the OD ratio at 260 and 280 nm, rises from 1.9 to 2.5, which indicates that contaminating proteins are removed by this method.

EXAMPLE 2

2.1.—This example describes a plasmid DNA purification experiment. Coupling of the oligonucleotide (5'-GAGGCTTCTTCTTCTTCTTCTTCTT-3' (SEQ ID No. 1)) to the column is performed as described in Example 1. For the coupling, the oligonucleotide is modified at the 5' end with an amine group linked to the phosphate of the spacer by an arm containing 6 carbon atoms (Modified oligonucleotide Eurogentec SA, Belgium). Plasmid pXL2563 was purified using the Wizard Megaprep kit (Promega Corp., Madison, Wis.) according to the supplier's recommendations. The buffers used in this example are the following:

Buffer F: 0–2 M NaCl, 0.2 M acetate, pH 4.5 to 5.
Buffer E: 1 M Tris-HCl pH 9, 0.5 mM EDTA.

The column is washed with 6 ml of buffer F, and 100 μg of plasmid pXL2563 diluted in 400 μl of buffer F are then applied to the column and incubated for 2 hours at room temperature. The column is washed with 10 ml of buffer F and elution is then carried out with buffer E. The plasmid is quantified by measuring optical density at 260 nm.

In this example, binding is carried out in a buffer whose molarity with respect to NaCl varies from 0 to 2 M (buffer F). The purification yield decreases when the molarity of NaCl falls. The pH of the binding buffer can vary from 4.5 to 5, the purification yield being better at 4.5. It is also possible to use another elution buffer of basic pH: elution was thus carried out with a buffer comprising 50 mM borate, pH 9, 0.5 mM EDTA.

2.2.—Coupling of the oligonucleotide (5'-GAGGCTTCTTCTTCTTCTTCTTCTT-3' (SEQ ID No. 1) to the column is carried out as described in Example 1. Plasmid pXL2563 was purified using the Wizard Megaprep kit (Promega Corp., Madison, Wis.) according to the supplier's recommendations. The buffers used in this example are the following:

Buffer F: 0.1 M NaCl, 0.2 M acetate, pH 5.

Buffer E: 1 M Tris-HCl pH 9, 0.5 mM EDTA.

The column is washed with 6 ml of buffer F, and 100 μg of plasmid pXL2563 diluted in 400 μl of buffer F are then applied to the column and incubated for one hour at room temperature. The column is washed with 10 ml of buffer F and elution is then carried out with buffer E. The content of genomic or chromosomal *E. coli* DNA present in the plasmid samples before and after passage through the oligonucleotide column is measured. This genomic DNA is quantified by PCR using primers in the *E. coli* galK gene. According to the following protocol: The sequence of these primers is described by Debouck et al. (Nucleic Acids Res. 1985, 13, 1841–1853):

5'-CCG AAT TCT GGG GAC CAA AGC AGT TTC-3' (SEQ ID No. 24)

and 5'-CCA AGC TTC ACT GTT CAC GAC GGG TGT-3' (SEQ ID No. 25).

The reaction medium comprises, in 25 μl of PCR buffer (Promega France, Charbonnières): 1.5 mM MgCl$_2$; 0.2 mM dXTP (Pharmacia, Orsay); 0.5 μM primer; 20 U/ml Taq polymerase (Promega). The reaction is performed according to the sequence:

5 min at 95° C.

30 cycles of 10 sec at 95° C.

30 sec at 60° C.

1 min at 78° C.

10 min at 78° C.

The amplified DNA fragment 124 base pairs in length is separated by electrophoresis on 3% agarose gel in the presence of SybrGreen I (Molecular Probes, Eugene, U.S.A.), and then quantified by reference to an Ultrapur genomic DNA series from *E. coli* strain B (Sigma, ref D4889).

There is 1% of chromosomal DNA in the sample applied to the column, and 0.2% in the sample purified on the oligonucleotide column.

EXAMPLE 3

Experiment on clear lysate

This example describes plasmid DNA purification from a clear lysate of bacterial culture, on the so-called "miniprep" scale: 1.5 ml of an overnight culture of DH5α strains containing plasmid pXL2563 are centrifuged, and the pellet is resuspended in 100 μl of 50 mM glucose, 25 mM Tris-HCl, pH 8, 10 mM EDTA. 200 μl of 0.2 M NaOH, 1% SDS are added, the tubes are inverted to mix, 150 μl of 3 M potassium acetate, pH 5 are then added and the tubes are inverted to mix. After centrifugation, the supernatant is recovered and loaded onto the oligonucleotide column obtained as described in Example 1. Binding, washes and elution are identical to those described in Example 1. Approximately 1 μg of plasmid is recovered from 1.5 ml of culture. The plasmid obtained, analysed by agarose gel electrophoresis and ethidium bromide staining, takes the form of a single band of "supercoiled" circular DNA. No trace of high molecular weight (chromosomal) DNA or of RNA is detectable in the plasmid purified by this method. The ratio of the optical densities at 260 and 280 nm is greater than 2.

EXAMPLE 4

4.1: This example describes a plasmid DNA purification experiment carried out under the same conditions as Example 3, starting from 20 ml of bacterial culture of DH5α strains containing plasmid pXL2563. The cell pellet is taken up in 1.5 ml of 50 mM glucose, 25 mM Tris-HCl, pH 8, 10 mM EDTA. Lysis is carried out with 2 ml of 0.2 M NaOH, 1% SDS, and neutralization with 1.5 ml of 3 M potassium acetate, pH 5. The DNA is then precipitated with 3 ml of 2-propanol, and the pellet is taken up in 0.5 ml of 0.2 M sodium acetate, pH 5, 0.1 M NaCl and loaded onto the oligonucleotide column obtained as described in Example 1. Binding, washing of the column and elution are carried out as described in Example 1, except for the washing buffer, the molarity of which with respect to NaCl is 0.1 M. Approximately 16 μg of plasmid DNA are obtained. The plasmid obtained, analysed by agarose gel electrophoresis and ethidium bromide staining, takes the form of a single band of "supercoiled" circular DNA. No trace of high molecular weight (chromosomal) DNA or of RNA is detectable in the purified plasmid. Digestion of the plasmid with a restriction enzyme gives a single band at the expected molecular weight of 3 kilobases. The protein concentration in the samples falls from 125 μg/ml in the clear lysate to less than 1 μg/ml in the purified plasmid (Micro-BCA assay, Pierce). The endotoxin concentration, estimated by LAL assay (Biosepra) is divided by a factor of greater than 10 in the purified plasmid, relative to the starting clear lysate.

4.2: The plasmid used contains a cassette containing the cytomegalovirus promoter, the gene coding for luciferase and the homopurine-homopyrimidine sequence $(GAA)_{17}$ originating from plasmid pXL2563. The strain DH1 (Maniatis et al., 1989) containing this plasmid is cultured in a 7-litre fermenter. A clear lysate is prepared from 200 grams of cells: the cell pellet is taken up in 2 litres of 25 mM Tris, pH 6.8, 50 mM glucose, 10 mM EDTA, to which 2 litres of 0.2 M NaOH, 1% SDS, are added. The lysate is neutralized by adding one litre of 3M potassium acetate. After diafiltration, 4 ml of this lysate are applied to a 5 ml HiTrap-NHS column coupled to the oligonucleotide of sequence 5'-GAGGCTTCTTCTTCTTCTTCTTCTT-3' (SEQ ID No. 1), according to the method described in Example 1.1. Washing and elution are carried out as described in Example 1. Approximately 400 micrograms of plasmid are recovered. The level of genomic DNA in this sample, measured by the technique described in Example 2.2, is 0.1%.

EXAMPLE 5

Use of a modified oligonucleotide

This example describes the use of an oligonucleotide bearing methylated cytosines. The sequence of the oligonucleotide used is as follows:

5'-GAGG$^{Me}$CTT$^{Me}$CTT$^{Me}$CTT$^{Me}$CTT$^{Me}$CTT$^{Me}$CTT$^{Me}$CTT-3' (SEQ ID No. 12)

This oligonucleotide possesses an NH$_2$ group at the 5' end. $^{Me}$C=5-methylcytosine. This oligonucleotide enables plasmid pXL2563 to be purified under the conditions of Example 1 with a binding buffer of pH 5 (the risk of degradation of the plasmid is thereby decreased).

EXAMPLE 6

In the above examples, the oligonucleotide used is modified at the 5'-terminal end with an amine group linked to the phosphate through an arm containing 6 carbon atoms: NH$_2$-(CH$_2$)$_6$. In this example, the amine group is linked to the phosphate of the 5'-terminal end through an arm containing 12 carbon atoms: NE$_2$-(CH$_2$)$_{12}$. Coupling of the oligonucleotide and passage through the column are carried out as described in Example 2 with a buffer F: 2 M NaCl, 0.2 M acetate, pH 4.5. This oligonucleotide makes it possible to have better purification yields: a 53% yield is obtained, whereas, with the oligonucleotide containing 6 carbon atoms, this yield is of the order of 45% under the same conditions.

EXAMPLE 7

Following the cloning strategy described in Example 1.2, another two plasmids carrying homopurine-homopyrimidine sequences were constructed: the plasmid pXL2725 which contains the sequence (GGA)$_{16}$, and the plasmid pXL2726 which contains the sequence (GA)$_{25}$.

EXAMPLE 7.1

Construction of the plasmids

Plasmids pXL2725 and pXL2726, analogous to plasmid pXL2563, were constructed according to the cloning strategy described in Example 1.2, using the following oligonucleotide pairs:
5986: 5'-GATCC(GA)$_{25}$GGG-3' (SEQ ID No. 13)
5987: 5'-AATTCCC(TC)$_{25}$G-3' (SEQ ID No. 14)
5981: 5'-GATCC(GGA)$_{17}$GG-3' (SEQ ID No. 15)
5982: 5'-AATT(CCT)$_{17}$CCG-3' (SEQ ID No. 16)

The oligonucleotide pair 5986 and 5987 was used to construct plasmid pXL2726 by cloning the oligonucleotides at the BamHI and EcoRI sites of pBKS+ (Stratagene Cloning System, La Jolla, Calif.), while the oligonucleotides 5981 and 5982 were used for the construction of plasmid pXL2725. The same experimental conditions as for the construction of plasmid pXL2563 were used, and only the oligonucleotide pairs were changed. Similarly, the cloned sequences were verified by sequencing on the plasmids. This enabled it to be seen that plasmid pXL2725 possesses a modification relative to the expected sequence: instead of the sequence GGA repeated 17 times, there is GGAGA (GGA)$_{15}$ (SEQ ID No. 17).

EXAMPLE 7.2

Preparation of the columns and Purification

The oligonucleotides forming triple helices with these homopurine sequences were coupled to HiTrap columns according to the technique described in Example 1.1. The oligonucleotide of sequence
5'-AATGCCTCCTCCTCCTCCTCCTCCT-3' (SEQ ID No. 18) was used for the purification of plas id pXL2725, and the oligonucleotide of sequence
5'-AGTGCTCTCTCTCTCTCTCTCTCTCT-3' (SEQ ID No. 19) was used for the purification of plasmid pXL2726.

The two columns thereby obtained enabled the corresponding plasmids to be purified according to the technique described in Example 2, with the following buffers:
Buffer F: 2 M NaCl, 0.2 M acetate, pH 4.5.
Buffer E: 1 M Tris-HCl, pH 9, 0.5 mM EDTA.
The yields obtained are 23% and 31% for pXL2725 and pXL2726, respectively.

EXAMPLE 8

This example illustrates the influence of the length of the specific sequence present in the plasmid on the purification yields.

EXAMPLE 8.1

Construction of the plasmids

The reporter gene used in these experiments to demonstrate the activity of the compositions of the invention is the gene coding for luciferase (Luc).

The plasmid pXL2621 contains a cassette containing the 661-bp cytomegalovirus (CMV) promoter, extracted from pcDNA3 (Invitrogen Corp., San Diego, Calif.) by cleavage with the restriction enzymes MluI and HindIII, cloned upstream of the gene coding for luciferase, at the MluI and HindIII sites, into the vector pGL basic Vector (Promega Corp., Madison, Wis.). This plasmid was constructed using standard techniques of molecular biology.

The plasmids pXL2727-1 and pXL2727-2 were constructed in the following manner:

Two micrograms of plasmid pXL2621 were linearized with BamHI; the enzyme was inactivated by treatment for 10 min at 65° C.; at the same time, the oligonucleotides 6006 and 6008 were hybridized as described for the construction of plasmid pXL2563.
6006: 5'-GATCT(GAA)$_{17}$CTGCAGATCT-3' (SEQ ID No. 20)
6008: 5'-GATCAGATCTGCAG(TTC)$_{17}$A-3' (SEQ ID No. 21)

This hybridization mixture was cloned at the BamHI ends of plasmid pXL2621 and, after transformation into DH5a, recombinant clones were identified by PstI enzymatic restriction analysis, since the oligonucleotides introduce a PstI site. Two clones were selected, and the nucleotide sequence of the cloned fragment was verified using the primer (6282, 5'-ACAGTCATAAGTGCGGCGACG-3' (SEQ ID No. 22)) as a sequencing reaction primer (Viera J. and J. Messing, 1982. The pUC plasmids an M13mp7-derived system for insertion mutagenesis and sequencing with synthetic universal primers. Gene 19:259–268).

The first clone (pXL2727-1) contains the sequence GAA repeated 10 times. The second (pXL2727-2) contains the sequence 5'-GAAGAAGAG(GAA)$_7$GGAAGAGAA-3' (SEQ ID No. 23).

EXAMPLE 8.2

Preparation of the columns and Purification

A column such as the one described in Example 1, and which is coupled to the oligonucleotide 5'-GAGGCTTCTTCTTCTTCTTCTTCTT-3' (SEQ ID No. 1), is used.

The plasmid pXL2727-1 carries 14 repeats of the sequence GAA. The oligonucleotide described above, which contains only 7 repeats of the corresponding hybridization sequence CTT, can hence hybridize with the plasmid at 8 different positions. Plasmid pXL2727-2, in contrast, possesses a hybridizing sequence (GAA)$_7$ of the sane length as that of the oligonucleotide bound to the column. This oligonucleotide can hence hybridize at only one position on pXL2727-2.

The experiment is identical to the one described in Example 2, with the following buffers:
Buffer F: 2 M NaCl, 0.2 M acetate, pH 4.5.
Buffer E: 1 M Tris-HCl, pH 9, 0.5 mM EDTA.
The purification yield is 29% with plasmid pXL2727-1 and 19% with pXL2727-2.

EXAMPLE 8.3 in vitro transfection of mammalian cells

The cells used are NIH 3T3 cells, inoculated on the day before the experiment into 24-well culture plates on the basis of 50,000 cells/well. The plasmid is diluted in 150 mM NaCl and mixed with the lipofectant RPR115335. A lipofectant positive charges/DNA negative charges ratio equal to 6 is used. The mixture is vortexed, left for ten minutes at room temperature, diluted in medium without foetal calf serum and then added to the cells in the proportion of 1 µg of DNA per culture well. After two hours at 37° C., 10% volume/volume of foetal calf serum is added and the cells are incubated for 48 hours at 37° C. in the presence of 5% of $CO_2$. The cells are washed twice with PBS and the luciferase activity is measured according to the protocol described (Promega kit, Promega Corp. Madison, Wis.) on a Lumat LB9501 luminometer (EG and G Berthold, Evry). Plasmid pXL2727-1, purified as described in Example 8.2, gives transfection yields twice as large as those obtained with the same plasmid purified using the Wizard Megaprep kit (Promega Corp. Madison, Wis.).

What is claimed is:

1. A method for purifying double-stranded DNA from a solution containing said DNA mixed with other components, consisting essentially of passing the solution through a support comprising a covalently coupled oligonucleotide capable of forming a triple helix with said DNA by hybridization with a specific sequence present in the said DNA.

2. The method according to claim 1, wherein the solution is a cell lysate.

3. The method according to claim 2, wherein the cell lysate is a clear lysate.

4. The method according to claim 1, wherein the double-stranded DNA is prepurified.

5. The method according to claim 1, wherein the specific sequence present in the DNA comprises a homopurine-homopyrimidine sequence.

6. The method according to claim 1, wherein the specific sequence has been introduced artificially into the double-stranded DNA.

7. The method according to claim 5, wherein the oligonucleotide comprises a poly(CTT) sequence and the specific sequence present in the DNA is a poly(GAA) sequence.

8. The method according to claim 5, wherein the oligonucleotide comprises the sequence GAGGCTTCTTCTTCT-TCTTCTTCTT (SEQ ID NO: 1).

9. The method according to claim 5, wherein the oligonucleotide comprises the sequence $(CTT)_7$ (SEQ ID NO: 26).

10. The method according to claim 8, wherein the specific sequence present in the DNA comprises the sequence $(GAA)_7$, $(GAA)_{14}$ or $(GAA)_{17}$.

11. The method according to claim 5, wherein the specific sequence present in the DNA comprises the sequence SEQ ID NO: 5 and the oligonucleotide comprises the sequence SEQ ID NO: 6 or SEQ ID NO: 7.

12. The method according to claim 5, wherein the specific sequence present in the DNA comprises the sequence SEQ ID NO: 17 and the oligonucleotide comprises the sequence SEQ ID NO: 18.

13. The method according to claim 5, wherein the specific sequence present in the DNA comprises the sequence $(GA)_{25}$ and the oligonucleotide comprises the sequence SEQ ID NO: 19.

14. The method according to claim 1, wherein the specific sequence is naturally present in the double-stranded DNA.

15. The method according to claim 14, wherein the specific sequence naturally present in the DNA is a homopurine-homopyrimidine sequence present in the origin of replication of a plasmid.

16. The method according to claim 15, wherein the specific DNA sequence comprises all or part of the sequence SEQ ID NO: 2.

17. The method according to claim 16, wherein the oligonucleotide comprises the sequence SEQ ID NO: 3.

18. The method according to claim 14, wherein the specific DNA sequence comprises all or part of the sequence SEQ ID NO: 4 or of the sequence SEQ ID NO: 8.

19. The method according to claim 1, wherein the oligonucleotide is coupled to the support through a disulphide, thioether, ester, amide or amine link.

20. The method according to claim 19, wherein the oligonucleotide is bound to the column via an arm comprised of a carbon chain $(CH_2)_n$ wherein n is an integer between 1 and 18 inclusive, the said arm being linked to the oligonucleotide through a phosphate and to the column through an amide link.

21. The method according to claim 20, wherein the arm comprises a linear carbon chain comprising 6 carbon atoms.

22. The method according to claim 20, wherein the arm is comprises of a linear carbon chain comprising 12 carbon atoms.

23. The method according to claim 1, wherein the oligonucleotide comprises at least one chemical modification making it resistant to or protected against nucleases, or increasing its affinity for the specific sequence.

24. The method according to claim 23, wherein the oligonucleotide comprises a homopyrimidine sequence comprising at least one methylated cytosine.

25. The method according to claim 1, wherein the DNA comprises one or more sequences of therapeutic importance.

26. The method according to claim 1, wherein the double-stranded DNA is a circular DNA.

27. The method according to claim 26, wherein the circular DNA is a plasmid.

28. The method according to claim 1, wherein the specific sequence present in the double-stranded DNA contains several positions for hybridization with the oligonucleotide.

29. The method according to claim 1, wherein the support is a functionalized chromatographic support, a functionalized plastic surface or functionalized latex beads.

30. The method according to claim 29, wherein the support is a functionalized chromatographic support.

31. The method according to claim 1, wherein the purified doubled-stranded DNA has a chromosomal DNA content of less than or equal to 0.5%.

32. The method according to claim 31, wherein the purified doubled-stranded DNA has a chromosomal DNA content of less than or equal to 0.2%.

33. The method according to claim 1, wherein the purified doubled-stranded DNA has a chromosomal DNA content of less than or equal to 0.1%.

34. A method for purifying double-stranded RNA from a solution containing said RNA mixed with other components, consisting essentially of passing the solution through a support comprising a covalently coupled oligonucleotide capable of forming a triple helix with said RNA by hybridization with a specific sequence present in the said RNA.

35. A method for the purification of plasmid DNA from a solution containing said DNA mixed with other components, consisting essentially of passing the solution through a support comprising a covalently coupled oligonucleotide capable of forming a triple helix with said DNA by hybridization with a specific sequence present in the said DNA.

36. The method according to claim 35, wherein the oligonucleotide comprises the sequence $(CTT)_n$, wherein n is an integer between 1 and 15 inclusive, and wherein the specific sequence present in the DNA comprises at least n complementary GAA units.

37. The method according to claim 36, wherein the specific sequence present in the DNA comprises n+1 complementary GAA units.

38. The method according to claim 36, wherein the specific sequence present in the DNA comprises n+10 complementary GAA units.

39. The method according to claim 35, wherein the oligonucleotide comprises the sequence $(CTT)_n$, wherein n is an integer between 1 and 15 inclusive, and wherein the specific sequence present in the DNA comprises at least n complementary GAA units.

40. The method according to claim 39, wherein the specific sequence present in the DNA comprises n+1 complementary GAA units.

41. The method according to claim 39, wherein the specific sequence present in the DNA comprises n+10 complementary GAA units.

* * * * *

UNITED STATES PATENT AND TRADEMARK OFFICE
CERTIFICATE OF CORRECTION

PATENT NO.   : 6,287,762 B1
DATED        : September 11, 2001
INVENTOR(S)  : Joel Crouzet et al.

It is certified that error appears in the above-identified patent and that said Letters Patent is hereby corrected as shown below:

Column 24,
Lines 38-39, "$(GA)_{25}$" should read -- $(GA)_{25}$ --.
Lines 65-66, "is comprises of" should read -- is comprised of --.

Column 26,
Line 10, "claim 35" should read -- claim 5 --.

Signed and Sealed this

Second Day of July, 2002

Attest:

JAMES E. ROGAN
Attesting Officer    Director of the United States Patent and Trademark Office

```
                        SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:1:

GAGGCTTCTT CTTCTTCTTC TTCTT                                          25

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:2:

CTTCCCGAAG GGAGAAAGG                                                 19

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:3:

GAAGGGTTCT TCCCTCTTTC C                                              21

(2) INFORMATION FOR SEQ ID NO:4:

(i) SEQUENCE CHARACTERISTICS:
        (A) LENGTH: 13 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:4:

GAAAAAGGAA GAG                                                          13

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:5:

AAGGGAGGGA GGAGAGGAA                                                    19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:6:

AAGGAGAGGA GGGAGGGAA                                                    19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:7:

TTGGTGTGGT GGGTGGGTT                                                    19

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:8:

AAAAAAGGGA ATAAGGG                                                      17

(2) INFORMATION FOR SEQ ID NO:9:

(i) SEQUENCE CHARACTERISTICS:

(A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:9:

GATCCGAAGA AGAAGAAGAA GAAGAAGAAG AAGAAGAAGA AGAAGAAGAA GAAGAAGG         58

(2) INFORMATION FOR SEQ ID NO:10:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:10:

AATTCCTTCT TCTTCTTCTT CTTCTTCTTC TTCTTCTTCT TCTTCTTCTT CTTCTTCG         58

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:11:

TGACCGGCAG CAAAATG                                                      17

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:12:

GAGGCTTCTT CTTCTTCTTC TTCTT                                             25

(2) INFORMATION FOR SEQ ID NO:13:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:13:

GATCCGAGAG AGAGAGAGAG AGAGAGAGAG AGAGAGAGAG AGAGAGAGAG AGAGAGGG         58

(2) INFORMATION FOR SEQ ID NO:14:

```
      (i) SEQUENCE CHARACTERISTICS:
          (A) LENGTH: 58 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO:14:

AATTCCCTCT CTCTCTCTCT CTCTCTCTCT CTCTCTCTCT CTCTCTCTCT CTCTCTCG        58

(2) INFORMATION FOR SEQ ID NO:15:

(i) SEQUENCE CHARACTERISTICS:
          (A) LENGTH: 58 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO:15:

GATCCGGAGG AGGAGGAGGA GGAGGAGGAG GAGGAGGAGG AGGAGGAGGA GGAGGAGG        58

(2) INFORMATION FOR SEQ ID NO:16:

(i) SEQUENCE CHARACTERISTICS:
          (A) LENGTH: 58 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO:16:

AATTCCTCCT CCTCCTCCTC CTCCTCCTCC TCCTCCTCCT CCTCCTCCTC CTCCTCCG        58

(2) INFORMATION FOR SEQ ID NO:17:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO:17:

GGAGAGGAGG AGGAGGAGGA GGAGGAGGAG GAGGAGGAGG AGGAGGAGGA                 50

(2) INFORMATION FOR SEQ ID NO:18:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO:18:

AATGCCTCCT CCTCCTCCTC CTCCT                                            25

(2) INFORMATION FOR SEQ ID NO:19:
```

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:19:

AGTGCTCTCT CTCTCTCTCT CTCTCT                                          26

(2) INFORMATION FOR SEQ ID NO:20:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:20:

GATCTGAAGA AGAAGAAGAA GAAGAAGAAG AAGAAGAAGA AGAAGAAGAA GAAGAACTGC      60

AGATCT                                                                66

(2) INFORMATION FOR SEQ ID NO:21:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:21:

GATCAGATCT GCAGTTCTTC TTCTTCTTCT TCTTCTTCTT CTTCTTCTTC TTCTTCTTCT      60

TCTTCA                                                                66

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:22:

ACAGTCATAA GTGCGGCGAC G                                               21

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:23:
```

-continued

```
GAAGAAGAGG AAGAAGAAGA AGAAGAAGAA GGAAGAGAA                         39

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:24:

CCGAATTCTG GGGACCAAAG CAGTTTC                                      27

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:25:

CCAAGCTTCA CTGTTCACGA CGGGTGT                                      27
```